United States Patent
Shmilowitz et al.

(10) Patent No.: US 9,326,519 B2
(45) Date of Patent: May 3, 2016

(54) FLOWABLE AND NON-DUSTING GRANULATED METHYLENE DITHIOCYANATE

(71) Applicant: BROMINE COMPOUNDS LTD., Beer Sheva (IL)

(72) Inventors: Shaul Shmilowitz, Meitar (IL); Xingye Wu, Lianyuangang (CN)

(73) Assignee: Bromine Compounds Ltd., Beer Sheva (IL)

(*) Notice: Subject to any disclaimer, the term of this patent is extended or adjusted under 35 U.S.C. 154(b) by 0 days.

(21) Appl. No.: 14/443,678

(22) PCT Filed: Nov. 25, 2013

(86) PCT No.: PCT/IL2013/050969
§ 371 (c)(1),
(2) Date: May 19, 2015

(87) PCT Pub. No.: WO2014/080407
PCT Pub. Date: May 30, 2014

(65) Prior Publication Data
US 2015/0282485 A1    Oct. 8, 2015

Related U.S. Application Data

(60) Provisional application No. 61/729,753, filed on Nov. 26, 2012.

(51) Int. Cl.
*A01N 47/46* (2006.01)
*A01N 47/48* (2006.01)
*A01N 25/12* (2006.01)
*B01J 2/22* (2006.01)
*C07C 331/04* (2006.01)

(52) U.S. Cl.
CPC ............... *A01N 47/46* (2013.01); *A01N 47/48* (2013.01); *B01J 2/22* (2013.01); *C07C 331/04* (2013.01); *Y10T 428/2982* (2015.01)

(58) Field of Classification Search
CPC ....... A01N 47/48; A01N 25/12; A01N 47/46; B01J 2/22; C07C 331/04; Y10T 428/2982
See application file for complete search history.

(56) References Cited

U.S. PATENT DOCUMENTS

| 4,849,134 A | 7/1989 | Georlette et al. |
| 6,200,586 B1 * | 3/2001 | Lambie ............... A01N 25/04 424/405 |
| 6,281,169 B1 * | 8/2001 | Yeoman .............. A01N 25/04 504/150 |

FOREIGN PATENT DOCUMENTS

CN    1080234 A    1/1994

OTHER PUBLICATIONS

International Search Report of a counterpart foreign application, 2 pages, Feb. 18, 2014.

* cited by examiner

*Primary Examiner* — Ernst V Arnold
(74) *Attorney, Agent, or Firm* — Roach Brown McCarthy & Gruber, P.C.; Kevin D. McCarthy

(57) ABSTRACT

This invention provides granulated methylene dithiocyanate for safe and environmentally friendly industrial antimicrobial use, and a process for manufacturing it.

12 Claims, No Drawings

FLOWABLE AND NON-DUSTING GRANULATED METHYLENE DITHIOCYANATE

FIELD OF THE INVENTION

The present invention relates to non-dusting solid forms of methylene dithiocyanate, a process for manufacturing them and their application.

BACKGROUND OF THE INVENTION

Methylene dithiocyanate, known also as methylene bis(thiocyanate), is a pesticide used broadly as an antibacterial, antifungal, and antialgal agent. The applications of the material (herein abbreviated MBT) include water cooling systems, paint manufacturing, metalworking cutting fluids, pulp and paper mills, oil drilling/mud fluids, fracturing, leather processing, latex paints, wood pressure treatments, wood protection treatments—including as a wood preservative stain to combat wood rot in residential areas. Available are various formulations, comprising diluted liquids. The MBT raw material is a powder solid under normal temperature, which is dusty and has tendency to cake. MBT is highly toxic, and its potential degradation products include cyanide and formaldehyde; therefore, the dermal contact or inhalation should be particularly avoided. Therefore, a need is felt for a safe concentrated solid form, making the transport of raw MBT and its handling safer and cheaper. It is therefore an object of the invention to provide a solid concentrated MBT, which would be granular without employing a binder.

It is a further object of this invention to provide a process for manufacturing a granular MBT without tendency to dust.

It is another object of this invention to provide a process for manufacturing a granular MBT without tendency to cake.

It is still another object of the invention to provide flowable and non-dusting solid MBT for direct use and/or for the preparation of solid and liquid formulations/mixtures, and for use in the oil & gas segment, in applications such as fracturing.

Other objects and advantages of present invention will appear as description proceeds.

SUMMARY OF THE INVENTION

The invention provides granulated methylene bis(thiocyanate) (MBT) comprising at least 97% MBT in the form of granules having dimensions between 0.2 mm and 20 mm. The granulated MBT according to the invention comprises particles having at least 87% of the MBT theoretical density. The granulated MBT according to the invention is preferably a freely flowing and non-dusting solid, preferably without tendency to caking.

The invention is directed to a method of controlling or preventing an infestation by various pests, particularly microbial pests, comprising employing the granulated MBT consisting of at least 97% MBT within granules exhibiting dimensions between 0.2 mm and 20 mm. The method according to the invention comprises employing said MBT in water cooling systems, in paint manufacturing, in metalworking cutting fluids, in pulp and paper mills, in oil & gas applications, fracturing, in drilling fluids, in leather processing, in latex paints, in wood protection treatments, and in wood pressure treatments. Said controlling or preventing an infestation by pests comprises one of the following activities: bactericide, bacteriostatic, fungicide, fungistatic, algaecide, or algaestatic.

The invention provides a process for manufacturing granulated methylene bis(thiocyanate) (MBT) comprising at least 97% MBT in the form of granules exhibiting dimensions between 0.2 mm and 20 mm, comprising i) delivering a powder containing at least 97% MBT and no binder to a screw feeder of a pelletizer, for example by a vacuum feeder; and ii) compacting said powder by two rollers under the force of the screw feeder, wherein the delivery pressure is at least 500 $kg/cm^2$ and preferably at least 1000 $kg/cm^2$. The process preferably comprises i) delivering a powder containing at least 97% MBT and no binder to a screw feeder of a pelletizer, for example by a vacuum feeder; ii) compacting said powder by two rollers, whereby obtaining a chunk, under the force of the screw feeder, wherein the delivery pressure is at least 1000 $kg/cm^2$ and preferably at least 1500 $kg/cm^2$; iii) crushing said chunk of MBT, whereby obtaining primary particles; and iv) screening said particles on a vibrating screen, whereby separating compacted MBT granules having dimensions of between 0.2 to 20 mm. In a preferred embodiment, the process of the invention comprises i) delivering a powder containing at least 97% MBT and no binder to a screw feeder of a pelletizer by a vacuum feeder; ii) compacting said powder by two rollers, whereby obtaining a chunk, under the force of the screw feeder, wherein the delivery pressure is at least 1500 $kg/cm^2$; iii) crushing said chunk of MBT, whereby obtaining primary particles; iv) screening said particles on a vibrating screen, whereby separating final compacted MBT granules having dimensions of between 0.2 to 20 mm; and v) returning the remaining MBT material, not included in the final granules, to the screw feeder by vacuum feeder. Said delivery pressure is up to 2500 $kg/cm^2$. The invention provides a process for manufacturing granulated methylene bis(thiocyanate) (MBT) exhibiting a density of at least 87% of the theoretical MBT solid density, comprising i) delivering a powder containing at least 97% MBT and no binder to a screw feeder of a pelletizer by a vacuum feeder; and ii) compacting said powder by two rollers under the force of the screw feeder, wherein the delivery pressure is at least 1500 $kg/cm^2$; iii) thereby obtaining a non-dusting solid MBT. In one embodiment of the invention, the process for manufacturing granulated methylene bis(thiocyanate) (MBT), the MBT exhibiting a density of at least 87% of the theoretical MBT solid density, for example at least 88% of the theoretical MBT solid density, comprises i) delivering a powder containing at least 97% MBT and no binder to a screw feeder of a pelletizer by a vacuum feeder; and ii) compacting said powder by two rollers under the force of the screw feeder, wherein the delivery pressure is at least 1500 $kg/cm^2$; thereby obtaining a solid MBT with lower tendency to caking.

DETAILED DESCRIPTION OF THE INVENTION

It has now been found that widely used pesticide MBT may be provided in a solid state in a non-dusty form without a binder and in a concentration approaching 100%. Methylene dithiocyanate can be compacted in a process of the invention without the addition of binders, fillers or any other additives.

The handling of the existing MBT solid material has required expensive safety precautions due to the hazardous nature of this biocide, especially in a fine powdered form; another problem in regard to the use of the available MBT solid material has been its tendency to create lumps, which has reduced the flowability and has caused handling and safety problems. The present invention solves the mentioned problems.

According to the invention, the powdered MBT can be transformed to granulated MBT (assay 98% min.) by the dry process without using any binders, fillers or additives. According to the invention, high quality granulated MBT is obtained under the delivery pressure of at least 500 kg/cm$^2$, preferably at least 1000 kg/cm$^2$, advantageously under the delivery pressure of at least 1500 kg/cm$^2$ of the rollers of the pelletizer.

This invention thus provides a method for preparing a safer form of MBT, which exhibits less dusting. The form, granular MBT, further exhibits lower tendency to aggregate to blocks and to cake. The MBT product of the invention is safer for workers' health and for the environment; the product has improved flowability and improved potential to be applied as such or to be further processed in preparation of diluted formulations, solid or liquid. The superior MBT form of the invention can be advantageously used in applications where dry dosing is needed, such as oil and gas drilling, mainly fracturing.

The instant invention provides MBT which is solid, concentrated, and easy to handle. In a preferred embodiment of the invention, the MBT product consists of at least 97% methylene dithiocyanate, and lacks a binder. Said product preferably comprises at least 98% MBT, and is in a form comprising pellets, granules tablets or briquettes.

Methylene dithiocyanate (MBT) in the form according to the invention will advantageously be used for controlling bacteria, algae, yeasts and fungi, for example in industrial water systems. Other applications include, for example, wood and leather preservation. MBT according to the invention will be also advantageously used in preparing formulations in organic solvents or as aqueous dispersions. Excellent penetrating powers of this pesticide makes it a preferred biocide in many applications, but the advantageous form of the invention will broaden its applications.

The technology of the invention can essentially yield a pure granulated MBT product, and in a preferred embodiment, the product is manufactured while comprising a pelletizer (compacting machine) without adding any binders, fillers or additives, which ensures that the use of the product will not be adversely affected by lowering the concentration of the active agent.

The technology of the invention can yield the dried pure granulated MBT, and the shape of the granules may be modified within the ambit of the present technology. Various shapes may be demanded in the market and they are obtainable from a pelletizer or a compacting machine within the scope of the invention. Both compaction granules and briquettes are made with a roll press. In one aspect, the compaction granules are made from loose material that has been compacted together (forming a chunk) and then broken apart, possibly in a granulator. In another aspect, briquettes or tablets are formed.

In one aspect of the invention, provided is a method of reducing pests comprising the use of granulated MBT of the invention, wherein the pests comprise at least one of viruses, bacteria, anaerobic bacteria, sulfate reducing bacteria, sulfide-producing bacteria, slime-forming bacteria, algae, fungi, fungi associated with sapstain or dry rot, surface mold, spoilage microorganisms, yeast, and parasites.

In one aspect of the invention, dusting raw material is compacted to particles of at least 87% of the MBT theoretical density. In a preferred embodiment, the granular MBT exhibits a density of at least 88% of the theoretical density. In other preferred embodiment, the granular MBT has a density corresponding to from 87 to 89% of the theoretical density.

The MBT granulated product of the invention will advantageously be incorporated directly, or after dissolving, or after dispersing, into products such as adhesives, coatings, fuels, metalworking cutting fluids, plastic products, resin emulsions, paints, paper products, oil & gas applications, fracturing and other industrial products.

In various modifications of pelletizing process, pelletizing may be done in a pellet mill, where feed is conditioned and thermally treated in the fitted conditioners of a pellet mill, the feed then being pushed through the holes and a pellet die, and exits the pellet mill as pelleted feed. Generally, dry granulation process aggregates the primary powder particles under high pressure, producing either a large tablet (slug) in a heavy duty tabletting press or, alternatively, the powder is squeezed between two rollers (roller compactor, chilsonator) to produce a sheet of squeezed material. In wet granulation, granules are formed by the addition of a liquid onto a powder bed which is under the influence of an impeller (in a high shear granulator), screws (in a twin screw granulator) or air (in a fluidized bed granulator). Once the solvent like methanol/water has been dried and the powders have formed a more densely held mass, then the material is milled. This process results in the formation of granules. The granular MBT of the invention may be obtained from various powders, when compacting under the delivery pressure of preferably more than 500 kg/cm$^2$, and still more preferably more than 1000 kg/cm$^2$, for example of about 1500 kg/cm$^2$, of the rollers of a pelletizer, possibly providing a chunk to be crushed and sieved. Higher compression, and bringing the granule density closer to the theoretical density (about 0.82) will provide higher granule stability.

The invention will be further described and illustrated by the following examples.

EXAMPLES

In one embodiment of the process according to the invention, MBT is compacted in accordance with the drawing and/or as described below.

High quality granulated MBT can be obtained when compacting under the delivery pressure of no less than 1500 kg/cm$^2$ of the rollers of a pelletizer, wherein the main steps include:

i) delivering an MBT powder to the screw feeder of a pelletizer for example by a vacuum feeder;

ii) the MBT powder is compacted to a chunk by two rollers under the force of the screw feeder;

iii) the chunk of MBT goes down to a crusher for crushing, whereby the MBT is crushed into mixture of greater particles and finer powder, and then the mixture goes through the vibration sieve, by which the particles of MBT are separated and collected; and iv) the final granules of MBT are packed as final product and the remaining MBT are re-delivered to the screw feeder by vacuum feeder until all the powdered MBT is granulated completely.

Because of MBT's irritating odor and its harmfulness to the eyes, the respiratory system and the skin of human being, it is important to keep the whole processing system in the suitable airproof condition. The pelletizer is preferably covered by an airproof frame, and the MBT powder is fed to the pelletizer through air-tight PP lines, avoiding dust escape to the open air. The end of the vacuum feeder and the airtight frame are preferably connected to the bag house via cyclone separator, and then to the scrubbing column. The bag house is cleaned periodically for MBT recovering; the absorption liquid in the column may be water, and MBT can be recovered to lower the costs and increase the yield. The MBT production according to the invention, thus, being a safe for human health and environmentally friendly.

Example 1

In three tests, a pelletizer under 3 different levels of the delivery pressures was employed: 1500 kg/cm$^2$, 2000 kg/cm$^2$, 2500 kg/cm$^2$, using the titanium alloy rollers with pencil shape, the size of the slots of the rollers was 1 mm×2.5 mm (width×depth), processing 50 kg raw powder in each test obtaining granules of the parameters as shown in Table 1:

TABLE 1

Parameters during manufacturing non-dusting solid MBT

| The delivery pressure of the rollers (kg/cm$^2$) | MBT granules | | | | |
|---|---|---|---|---|---|
| | density (g/cm$^3$) | crushing strength (kg/cm$^2$) | length (mm) | thickness (mm) | weight (mg) |
| 1500 | 0.721 | 30.0-80.0 | 4.0-12.0 | 0.5-1.5 | 10.0-50.0 |
| 2000 | 0.725 | 30.0-80.0 | 4.0-12.0 | 0.5-1.5 | 10.0-50.0 |
| 2500 | 0.731 | 30.0-80.0 | 4.0-12.0 | 0.5-2.0 | 10.0-60.0 |

Example 2

The production of the granulated MBT was performed by processing 500 kg powder containing about 98.5% MBT, the diameter of the holes of the crushing screen was 8 mm, the delivery pressure being 1500 kg/cm$^2$. The granulated MBT product was obtained without any aid of binders, fillers or additives, yielding 490 kg of 4-12 mm high quality granules of MBT obtained.

While the invention has been described using some specific examples, many modifications and variations are possible. It is therefore understood that the invention is not intended to be limited in any way, other than by the scope of the appended claims.

The invention claimed is:

1. Granulated methylene bis(thiocyanate) (MBT) comprising
   i) at least 97% MBT; and
   ii) granules exhibiting dimensions between 0.2 mm and 20 mm.

2. Granulated MBT according to claim 1, comprising particles having at least 87% of the MBT theoretical density.

3. Granulated MBT according to claim 1, being freely flowing and non-dusting solid, without tendency to caking.

4. A method of controlling or preventing an infestation by pests, comprising employing the granulated MBT of claim 1.

5. The method according to claim 4, comprising employing said MBT in water cooling systems, in paint manufacturing, in metalworking cutting fluids, in pulp and paper mills, in oil & gas applications, fracturing, in drilling fluids, in leather processing, in latex paints, in wood protection treatments, and in wood pressure treatments.

6. The method according to claim 4, wherein said controlling or preventing an infestation by pests comprises one of the following MBT activities: bactericide, bacteriostatic, fungicide, fungistatic, algaecide, or algaestatic.

7. A process for manufacturing granulated methylene bis (thiocyanate) (MBT) of claim 1, comprising
   i) delivering a powder containing at least 97% MBT and no binder to a screw feeder of a pelletizer by a vacuum feeder; and
   ii) compacting said powder by two rollers under the force of the screw feeder, wherein the delivery pressure is at least 500 kg/cm$^2$ and preferably at least 1000 kg/cm$^2$.

8. The process of claim 7, comprising
   i) delivering a powder containing at least 97% MBT and no binder to a screw feeder of a pelletizer by a vacuum feeder;
   ii) compacting said powder by two rollers, whereby obtaining a chunk, under the force of the screw feeder, wherein the delivery pressure is at least 1000 kg/cm$^2$ and preferably at least 1500 kg/cm$^2$;
   iii) crushing said chunk of MBT, whereby obtaining primary particles; and
   iv) screening said particles on a vibrating screen, whereby separating compacted MBT granules having dimensions of between 0.2 to 20 mm.

9. The process of claim 7, comprising
   i) delivering a powder containing at least 97% MBT and no binder to a screw feeder of a pelletizer by a vacuum feeder;
   ii) compacting said powder by two rollers, whereby obtaining a chunk, under the force of the screw feeder, wherein the delivery pressure is at least 1500 kg/cm$^2$;
   iii) crushing said chunk of MBT, whereby obtaining primary particles;
   iv) screening said particles on a vibrating screen, whereby separating final compacted MBT granules having dimensions of between 0.2 to 20 mm; and
   v) returning the remaining MBT material, not included in the final granules, to the screw feeder by vacuum feeder.

10. The process of claim 7, wherein said delivery pressure is up to 2500 kg/cm$^2$.

11. The process of claim 7, comprising
   i) delivering a powder containing at least 97% MBT and no binder to a screw feeder of a pelletizer by a vacuum feeder; and
   ii) compacting said powder by two rollers under the force of the screw feeder, wherein the delivery pressure is at least 1500 kg/cm$^2$;
thereby obtaining a non-dusting solid MBT, exhibiting a density of at least 87% of the theoretical MBT solid density.

12. The process of claim 7, comprising
   i) delivering a powder containing at least 97% MBT and no binder to a screw feeder of a pelletizer by a vacuum feeder; and
   ii) compacting said powder by two rollers under the force of the screw feeder, wherein the delivery pressure is at least 1500 kg/cm$^2$;
thereby obtaining a solid MBT with lower tendency to caking, exhibiting a density of at least 87% of the theoretical MBT solid density.

* * * * *